(12) United States Patent
Saylik et al.

(10) Patent No.: US 9,265,249 B2
(45) Date of Patent: Feb. 23, 2016

(54) DISPERSANTS IN HIGH-ELECTROLYTE SOLUTIONS

(75) Inventors: Dilek Saylik, Meadow Heights (AU); Rodney Walter Parr, Doncaster (AU); Bassam Tannir, Everberg (BE); Karen Van der Sande, Kortrijk-Dutsel (BE)

(73) Assignee: HUNTSMAN CORPORATION AUSTRALIA PTY LIMITED, Brooklyn, Victoria (AU)

( * ) Notice: Subject to any disclaimer, the term of this patent is extended or adjusted under 35 U.S.C. 154(b) by 243 days.

(21) Appl. No.: 13/318,084

(22) PCT Filed: May 7, 2010

(86) PCT No.: PCT/AU2010/000535
§ 371 (c)(1),
(2), (4) Date: Nov. 30, 2011

(87) PCT Pub. No.: WO2010/127408
PCT Pub. Date: Nov. 11, 2010

(65) Prior Publication Data
US 2012/0071321 A1    Mar. 22, 2012

Related U.S. Application Data (60) Provisional application No. 61/176,415, filed on May 7, 2009.

(51) Int. Cl.
| | | |
|---|---|---|
| A01N 25/30 | (2006.01) | |
| A01N 25/04 | (2006.01) | |
| A01N 57/20 | (2006.01) | |
| A61K 9/10 | (2006.01) | |
| A61K 47/48 | (2006.01) | |
| A01N 43/70 | (2006.01) | |

(52) U.S. Cl.
CPC ........... *A01N 25/30* (2013.01); *A01N 25/04* (2013.01); *A01N 43/70* (2013.01); *A01N 57/20* (2013.01); *A61K 9/10* (2013.01); *A61K 47/48238* (2013.01)

(58) Field of Classification Search
CPC ....... A01N 25/30; A01N 25/04; A01N 57/20; A01N 43/70; A61K 9/10; A61K 47/48238
USPC ........................................................ 504/103
See application file for complete search history.

(56) References Cited

U.S. PATENT DOCUMENTS

| | | |
|---|---|---|
| 3,799,758 A | 3/1974 | Franz |
| 4,336,835 A | 6/1982 | Takagishi et al. |
| 4,397,676 A | 8/1983 | Bakel |
| 5,773,026 A | 6/1998 | Schlipalius |
| 6,165,939 A | 12/2000 | Agbaje et al. |
| 6,569,809 B1 * | 5/2003 | Sato et al. ............ 504/127 |
| 6,849,577 B1 | 2/2005 | Bean et al. |
| 2002/0183206 A1 | 12/2002 | Jimoh |
| 2005/0101488 A1 | 5/2005 | Tanedani |
| 2007/0179270 A1 * | 8/2007 | Mock-Knoblauch et al. ........... 528/310 |

FOREIGN PATENT DOCUMENTS

| | | |
|---|---|---|
| EP | 0 088 180 | 9/1983 |
| EP | 0 343 142 | 11/1989 |
| GB | 2 108 115 | 5/1983 |
| WO | WO 99/45780 | 9/1999 |
| WO | 0159213 | 8/2001 |

OTHER PUBLICATIONS

EP Supplementary Search Report for Application No. EP 10 77 1910 dated Aug. 14, 2013.

* cited by examiner

*Primary Examiner* — John Pak
*Assistant Examiner* — Andriae M Holt
(74) *Attorney, Agent, or Firm* — Huntsman International LLC (57) ABSTRACT

Embodiments of the present invention disclose a composition of an electrolyte solution comprising a water-soluble active ingredient; a water-insoluble solid active ingredient; and a dispersant that consists of a polyaminoamide resin, a polyoxyalkylene derivative thereof, a polyglycerol derivative thereof, a polycarbamate derivative thereof and a combination thereof.

8 Claims, 3 Drawing Sheets

DISPERSANTS IN HIGH-ELECTROLYTE SOLUTIONS

CROSS-REFERENCE TO RELATED APPLICATIONS

This application is the National Phase of International Application PCT/AU2010/000535 filed May 7, 2010 which designated the U.S. and which claims priority to U.S. Provisional App. Ser. No. 61/176,415 filed May 7, 2009. The noted applications are incorporated herein by reference.

BACKGROUND

1. Field of the Invention

The present invention relates generally to dispersants, and in particular, polyamide dispersants for use in high-electrolyte agricultural solutions.

2. Description of the Related Art

The active ingredients in many agricultural applications are largely hydrophobic or water-insoluble in character and are, by necessity, often administered as finely divided solids suspended in aqueous media. The majority of these active ingredients are manufactured and marketed in concentrated forms which are then diluted prior to application. For example, the active ingredient is typically available in the form of a Suspension Concentrate (SC), Wettable Powder (WP) or Water Dispersible Granule (WG). Although solid formulations such as WP's and WG's are attractive not only from a loading delivery viewpoint, but also from an Occupational Health and Safety viewpont, not all agrochemicals can be formulated into solid formulations. Therefore liquid formulations such as SC's are an important formulation type. The addition of a suitable dispersant in SC formulations is essential in order to achieve a homogenous dispersion. Furthermore, once a homogenous dispersion is achieved, the resulting suspension must remain stable for sufficient time, at least, to allow application by usual means such as spraying. Any settling, agglomeration or flocculation of the solid in the SC formulation may lead to inconsistent and ineffective application as well as blockage of the spraying equipment. It is therefore necessary to provide a dispersant, which gives easy and homogenous dispersion and results in a suspension, which maintains its stability during prolonged storage or storage at elevated temperatures.

It is often desirable to suspend a water-insoluble solid active ingredient in a high-electrolyte (salt) solution, such as a fertilizer or particularly in the case of agrochemical formulations, to combine two active ingredients together in one formulation where one of the active ingredients is a solid dispersion while the other is an electrolyte solution. Solid dispersions in SC formulations in agrochemical applications are generally made using conventional dispersants such as ethylene oxide/propylene oxide block copolymers, tristyrylphenol ethoxylate derivatives, naphthelene suphonate condensate salts, and polymeric comb co-polymers, polyarylsulphonate condensates, alkylether phosphates and ether sulphates, and lignosulphonates. Although these dispersants afford stable SC's exhibiting no sign of sedimentation or crystal growth in non-electrolyte solutions, they fail as dispersants at high electrolyte solutions, leading to particle agglomeration and flocculation.

In some high-electrolyte solutions, lignosulfonates have been utilized as dispersants, however, they display poor dispersing properties. Large amounts of the dispersant are required in order to obtain a stable dispersion, which increases the cost of the dispersion. Furthermore, in higher electrolyte concentrations, or alternatively when high levels of the water insoluble active is required in the electrolyte solution, lignosulfonates fail to prevent particle agglomeration and flocculation.

BRIEF SUMMARY OF THE INVENTION

Embodiments of the claimed invention disclose the use of polyaminoamide resins and derivatives thereof as dispersants, providing improved dispersibilty and suspensibility in high-electrolyte solutions, as well as a number of other ancillary benefits, which will be more fully described herein.

In a first aspect, embodiments of the present invention disclose a composition comprising an electrolyte solution comprising a water-soluble active ingredient, a water-insoluble solid active ingredient, and a dispersant selected from the group consisting of: a polyaminoamide resin, a polyoxyalkylene derivate thereof, a polyglycerol derivative thereof, a polycarbamate derivative thereof and a combination thereof.

In an embodiment of the present invention, the concentration of the water-soluble active ingredient is greater than about 3% by weight of the composition.

In an embodiment of the present invention, the composition is an agricultural or veterinarian composition.

In an embodiment of the present invention, the water-insoluble active ingredient is at least one ingredient selected from the group consisting of: a pesticide, a herbicide, an insecticide, an insect repellent, a fungicide, a bactericide, a plant growth regulator, a fertilizer, an acaricide, an anthelmintic, a nematicide, and a combination thereof.

In an embodiment of the present invention, the polyaminoamide resin is obtained by thermal condensation of a poly-functional fatty acid with a poly-functional amine and wherein a starting acid for the poly-functional fatty acid is a $C_2$ to about a $C_{60}$ fatty acid.

In an embodiment of the present invention, the poly-functional amine is selected from the group consisting of: a $C_2$ to a $C_{10}$ alkylene diamine, a dimer diamine, a polyoxyalkyleneamine, an ethyleneamine and a combination thereof.

In an embodiment of the present invention, the ethyleneamine is selected from the group consisting of: an ethylenediamine, a diethylenetriamine, a triethylenetetramine, a tetraethylenepentaime and a combination thereof.

In an embodiment of the present invention, the polyoxyalkylene derivative is obtained by an alkoxylation reaction.

In an embodiment of the present invention, the polycarbamate derivative is obtained by a carbamation reaction.

In an embodiment of the present invention, the polyglycerol derivative is obtained by a glycidation reaction.

In an embodiment of the present invention, the polyoxyalkylene derivative is obtained by reacting the polyaminoamide resin with a compound selected from the group consisting of: an ethylene oxide, a propylene oxide, a butylene oxide and a combination thereof.

In an embodiment of the present invention, the polycarbamate derivative is obtained by reacting the polyaminoamide resin with a glycerin carbonate.

In an embodiment of the present invention, the polyglycerol derivative is obtained by reacting the polyaminoamide resin with a compound selected from a group consisting of: a glycidol, a glycerol, an epichlorohydrin and a combination thereof.

In an embodiment of the present invention, the ratio of the dispersant to the water-insoluble solid active ingredient is by weight from about 1:50 to about 1:5.

In an embodiment of the present invention, the ratio of the electrolyte in solution to the water-insoluble solid active ingredient is by weight from about 60:1 to about 1:1.

In an embodiment of the present invention, the composition further comprises at least one additive selected from the group consisting of: a humectant, a thickener, a wetting agent, an adjuvant, a stabilizer, a safener, a structuring agent, an antifoam, a pigment, a dye, a stench, an emetic, a filler, a carrier, a buffer and a combination thereof.

In a second aspect, embodiments of the present invention disclose a method for preparing a composition comprising the step of: contacting an electrolyte solution comprising a water-soluble active ingredient to a water-insoluble solid active ingredient and a dispersant selected from the group consisting of: a polyaminoamide resin, a polyoxyalkylene derivative thereof, a polyglycerol derivative thereof, a polycarbamate derivative thereof and a combination thereof.

In a third aspect, embodiments of the present invention disclose a method of treatment of vegetation comprising the step of contacting the composition of the present invention to vegetation or soil.

In a fourth aspect, embodiments of the present invention disclose a method of treatment of an animal comprising the step of contacting the composition of the present invention to the animal.

In a fifth aspect, embodiments of the present invention disclose a method of treatment of a substrate comprising the step of contacting the composition of the present invention to the substrate.

BRIEF DESCRIPTION OF THE DRAWINGS

The following figures have been added to further clarify properties of the present invention.

DETAILED DESCRIPTION OF THE INVENTION

Embodiments of the present invention disclose the use of polyaminoamide resins, polyalkoxyalkylene oxide derivatives thereof, polyglycerol derivatives thereof and polycarbamate derivatives thereof or combinations thereof as dispersants for the preparation of stable suspensions of water-insoluble solid active ingredients in high-electrolyte solutions. Embodiments of the present invention remain fluid and homogenous. Embodiments of the present invention typically exhibit no sign of particle agglomeration or flocculation. As a further advantage, these dispersants may display adjuvancy properties and thus may have a dual purpose in suspending the water-insoluble solid active ingredient and enhancing the biological effect of at least one of the active ingredients. Embodiments of the present invention can be used to formulate agricultural, veterinarian, public health or domestic compositions.

Embodiments of the present invention discloses a composition that includes: an electrolyte solution comprising a water-soluble active ingredient; a water-insoluble solid active ingredient; and a dispersant that is a polyaminoamide resin or a derivative thereof.

Embodiments of the present invention include an electrolyte solution. An electrolyte solution is normally formed when a salt (or an acid or base may be used) is placed into a solvent such as water and the individual components (ions) of the salt dissociate. The water-soluble active ingredient of the present invention, such as a salt, in a solvent such as water, may form this electrolyte solution. Electrolyte solutions of the present invention may be described as high-electrolyte if it has a high concentration of ions. Embodiments of the present invention include an electrolyte solution wherein the concentration of the water-soluble active ingredient is greater than about 3% by weight of the composition or equivalent ionic strength of the other water-insoluble solid active ingredients or a combination of dissolved salts. In other embodiments, the concentration of the water-soluble active ingredient is greater than about 4% by weight of the composition. In other embodiments, the concentration of the water-soluble active ingredient is greater than about 5% by weight of the composition. In other embodiments, the concentration of the water-soluble active ingredient is greater than about 10% by weight of the composition. In further embodiments, the concentration of the water-soluble active ingredient may be from about 10% by weight to about 70% by weight. In other embodiments, the concentration of the water-soluble active ingredient may be from about 15% by weight to about 40% by weight.

In embodiments where a high-electrolyte solution is desired, the water-soluble active ingredient may be in any concentration higher than about 30 g/L (as acid equivalent). In other embodiments, the water-soluble active ingredient may be in a concentration of about 120 g/L, 150 g/L, 360 g/L, 420 g/L, 450 g/L, 480 g/L, 490 g/L, 510 g/L, 517 g/L or 520 g/L. In one embodiment, the water-soluble active ingredient is in a concentration of about 540 g/L. In other embodiments, the concentration may be about 600 g/L.

Embodiments of the present invention include a water-soluble active ingredient. The water-soluble active ingredient in some embodiments may be a biologically active ingredient (as described later) such as a pesticide, in particular a herbicide. The water-soluble active ingredient can include but is not limited to, N-(phosphonomethyl) glycine (glyphosate) and salts thereof, 4-[hydroxyl(methyl)phosphinoyl]-DL-homoalanine (glufosinate) ammonium salts and other water soluble herbicides such as dicamba, amitrole, bromoxynil, and salts thereof, bipyridinium herbicides such as paraquat and diquat and salts thereof, amitrol, aromatic acid herbicides such as 2,4-D, MCPA (4-chloro-2-methylphenoxyacetic acid) and MCPB (4-(4-chloro-2-methylphenoxy)butanoate) and salts thereof, pyridine herbicides such as triclopyr and pichloram and salts thereof. Other examples of water-soluble ingredients suitable for use in the composition of the claimed invention include liquid fertilizers such as ammonium sulfate and plant growth regulators which may be gibberellins such as $GA_3$ and salts thereof. "Glyphosate" means any form of glyphosate, which in aqueous solution provides glyphosate anions along with suitable cations or glyphosate acid. Examples of such suitable cations are alkali metal cations, for instance sodium, potassium, ammonium and substituted ammonium cations. The latter include cations derived from primary or secondary amines such as isopropylamine, monoethanolamine or dimethylamine, and from diamines such as ethylenediamine. Other agriculturally acceptable salts of glyphosate are disclosed in U.S. Pat. No. 3,799,758. Further, examples of agriculturally acceptable salts of glyphosate are trimethyl-sulfonium salts ("sulfosate") or aminoguanidine salts as disclosed in EP-A-0 088 180. Because glyphosate has more than one replaceable hydrogen atom, mono- and di-salts are possible, as well as mixtures of such salts. Typical glyphosate salts are the potassium, ammonium and trimethylsulphonium salts as well as the mixed alkylsulfonium salts and trialkylammonium salts. The water-soluble active ingredient may also include other suitable active salts, bases, and acids. Other suitable biologically active ingredients may include micronutrients. Such micronutrients may be powders suspended in fertilizer formulations. One skilled in the art will recognize other appropriate water-soluble active ingredients to use in embodiments of the present invention.

Embodiments of the present invention include a water-insoluble solid active ingredient. Suitable water-insoluble solid active ingredients for use in the present invention include, but are not limited to, insecticides, insect repellents, fungicides, bactericides, herbicides, plant growth regulators, fertilizers, micronutrients, acaricides, anthelmintics, and nematicides. Suitable water-insoluble solid active ingredients typically have a water solubility profile of about 1.0% or less by weight of the composition at the temperature of 20° C. Examples of suitable solid pesticides include but are not limited to triazine herbicides such as atrazine, simazine, prometryn, ametryn, terbutryn and terbuthylazine, urea herbicides such as diuron, fluometuron and linuron, carbamates such as 1-naphthyl methylcarbamate, fungicides such as procymidone and mancozeb, acetimides such as cymoxanil, synthetic pyrethroids such as bifenthrin and alpha-cypermethrin, thiabendazole, carbendazim, copper oxychloride, thidiazuron, carbofuran, sulfur, chlorothalonil, tralkoxydim, triadimefon, calcium carbonate, imidacloprid, thiocloprid, captan, diflubenzuron, fipronil, metsulfuron-methyl, diflufenican, trifloxystrobin, triasulfuron, chlorsulfuron and metribuzin. A list of such water-insoluble solid active ingredients can be drawn from the Pesticide Dictionary (contained in the Farm Chemicals Handbook) or the British Crop Protection Society: Pesticides Manual. One skilled in the art, with the benefit of this disclosure, will recognize other suitable water-insoluble solid active ingredients to use in embodiments of the present invention.

Embodiments of the present invention include a dispersant. The dispersant may be selected from polyaminoamide resins, polyoxyalkylene derivates thereof, polyglycerol derivatives thereof, polycarbamate derivatives thereof and combinations thereof. The polyaminoamide resins are composed of a poly-functional dimer fatty acid grafted and/or crosslinked with a compound having amino groups. The polyaminoamide resins can be obtained by well-known methods, such as thermal condensation of any poly-functional fatty acids with any poly-functional amines. An example of a commercially suitable polyaminoamide resin is VERSAMID® polyaminoamides, which is a brand of resin available from Cognis GmbH. The polyaminoamide resin and its derivatives as described in the claimed invention may have, but are not limited to, the general structure outlined in Formula 1.

Formula 1: One possible structure of polyaminoamide resin and derivatives thereof In Formula 1, $R^1$ is a poly-functional dimer fatty acid wherein the starting acid is a $C_2$ to about $C_{60}$ fatty acid. $R^2$ and $R^3$ are either hydrogen or methyl groups or combinations thereof. $R^4$ is a hydrogen, methyl, alkyl or aryl group. X can be either oxygen or nitrogen, while Y can be either hydrogen or any ethylene oxide group, propylene oxide group, butylene oxide group or combinations thereof. In other implementations, Y can be any alkyl, alkylketone or glycerol group. Further, a is an integer from 1 to about 11, b is an integer from 0 to about 30, d is an integer from 1 to about 30, e is an integer from 0 to 1 and L is an integer from 1 to about 50.

The polyaminoamide derivatives as depicted in Formula 1 can be obtained by derivatization of a polymer backbone of a commercially available resin such as VERSAMID® polyaminoamides. Non-limiting examples of such derivatization reactions are shown in Schemes 1-3. Derivatization may be carried out either by an alkoxylation reaction (as shown in Scheme 1), a glycidation reaction (as shown in Scheme 2), or a carbamation reaction (as shown in Scheme 3).

Scheme 1: Polyaminoamide Resin ---(ethylene oxide)---> polyoxyalkylene derivate thereof Scheme 2: Polyaminoamide Resin ---(glycidol)---> polyglycerol derivate thereof Scheme 3: Polyaminoamide Resin ---(glycerin carbonate)---> carbamate derivate thereof The polyaminoamide derivatives compiled in Table 1 are composed of polyoxyalkylene oxide derivatives thereof, polyglycerol derivatives thereof and polycarbamate derivatives thereof that is further added to the polymer skeleton of the polyaminoamide resin. Those skilled in the art can readily obtain a number of polyaminoamide resins by changing the ratio of acid to amine, the degree of condensation (for example, the reaction time and temperature), as well as the compositions of the poly-functional acids or the poly-functional amines.

Further, the poly-functional amines used in the preparation of the polyaminoamide resins include any $C_2$ to about $C_{10}$ alkylene diamines; for example, hexamethylene diamine, 1,3-diaminopropane, 1,4-diaminobutane, piperazine, dipiperidyl propane and combinations thereof. The diamines used to prepare the polyaminoamide resins can be derived from any dimer fatty acids and the diamines can include primary amino groups instead of carboxyl groups. Such substances are often called dimer diamines. They are obtained by nitrile formation from dimerized fatty acids and subsequent hydrogenation. Polyoxyalkyleneamines, such as JEFFAMINE® polyoxyalkyleneamines that are commercially available from the Huntsman Corporation of The Woodlands, Tex. may also be used. Other preferred amines include ethyleneamines such as ethylenediamine, diethylenetriamine, triethylenetetramine, tetraethylenepentamine and combinations thereof. Moreover, the amines could be of any structure or dendrite and can be condensed with the fatty acids to result in the polyaminoamide resin according to the claimed invention.

The starting acids for the preparation of poly-functional dimer fatty acids used in the preparation of the polyaminoamide resin include any $C_2$ to about $C_{60}$ fatty acids such as oleic acid and linoleic acid that are found in tall oil fatty acids. These fatty acids may be polymerized by various catalytic and non-catalytic polymerization procedures to obtain the poly-functional dimer fatty acids.

In other embodiments, the polyaminoamide derivatives can be formed by reacting polyaminoamide resins with any of ethylene oxide, propylene oxide, butylene oxide, or combinations thereof to obtain water-soluble or water dispersible dispersing agents. In yet another example, the polyaminoamide resin can be reacted with glycerine carbonate, glycerol, glycidol or epichlorohydrin to obtain water-soluble polymeric dispersing agents. The polyaminoamide resins or derivatives formed by any of the above-mentioned methods has a preferable molecular weight from about 500 to about 500,000 Daltons. In other embodiments, the polyaminoamide resins or derivatives thereof have a molecular weight from about 500 to 50,000 Daltons. One skilled in the art, with the benefit of this disclosure, will recognize other suitable dispersants to use in embodiments of the present invention.

Typical ratios of the dispersant to the water-insoluble solid active ingredient by weight is from about 1:50 to about 1:5, more preferably from about 1:20 to about 1:10 and most preferably from about 1:20 to about 1:5. Additionally, the typical ratio of the electrolyte to the suspended water-insoluble solid active ingredient by weight is from about 60:1 to about 1:1, more preferably from about 5:1 to about 1:1 and most preferably from about 2:1 to about 1:1. One skilled in the art, with the benefit of this disclosure, will recognize suitable ratios to use depending on the application.

Embodiments of the present invention may also include one or more additives. Additives may include humectants such as propylene glycol, monoethylene glycol or glycerol which can also act as antifreeze agents, structuring agents such as silicas, for example AEROSIL® fumed silica (commercially available from Evonik Degussa GmbH) or clays, and thickeners such as xantham gums or other polysaccharide gums. Moreover, adjuvants which can further enhance the efficacy of the composition can be added, which may include, but are not limited to, non-ionic surfactants such as alkyl polysaccharides, alcohol ethoxylates, ethylenediamine alkoxylates and alkyl phenol ethoxylates or adjuvant belonging to the betaine class of chemistry may also be present. Other additives that may be used in agricultural applications include fillers and carriers such as natural and synthetic silicates and silicate minerals, mineral oxides and hydroxides and also natural and synthetically derived organic materials. Such materials may be added as porous carriers or simply to fill a formulation to a convenient weight. Examples of such fillers may include natural silicates such as diatomacious earth, synthetic precipitated silicas, clays such as kaolin, attapulgites and bentonites, zeolites, titanium dioxide, iron oxides and hydroxides, aluminium oxides and hydroxides, or organic materials such as bagasse, charcoal, or synthetic organic polymers.

Further, the compositions of the present invention may include other additives such as buffers, for example, disodium hydrogen phosphate and citric acid, an emetic, a stench, a safener and antifoam agents such as silicon antifoam, dyes and/or pigments.

In one embodiment, another additive can be used in combination with the dispersants of the claimed composition, such as a wetting agent; for example, an alkyl phenol ethoxylate or alkoxylate, an alkyl sulphate, alkylsulphonate or alkylethersulphate, fatty alcohol ethoxylate or alkoxylate, an alkyl etherphosphate ester, an ethoxylated sorbitan ester, a dialkylsulphosuccinate salt, a naphthalene sulphonate and high molecular weight alcohol alkoxylates. One skilled in the art, with the benefit of this disclosure, will recognize other appropriate additives to use depending on the use and application of the composition.

Embodiments of the present invention may exhibit adjuvancy properties that enhance the efficiency of at least one of the active ingredients. It is desirable that herbicides such as for example glyphosate and its salts, glufosinate and its salts, 2,4-D and its salts and paraquat and its salts include an adjuvant to enhance the deposition and uptake of the molecule in an active site within a plant. Herbicide adjuvancy is generally measured by field tests for broadleaf and grass weed species and it has been found that the described polyaminoamide derivatives function well compared to current industry standards, which include ROUNDUP® CT broadacre herbicide (containing glyphosate) that is commercially available from the Monsanto Company of St. Louis, Mo. (refer to Table 3 for bioefficacy results). Polyaminoamide resins or polyaminoamide derivatives can be used as adjuvants at about 5% weight per volume (w/v) to about 20% w/v, more typically at about 8% w/v to about 12% w/v and optionally for comparison to industry standards at about 8% w/v to about 10% w/v. The polyaminoamide resins or polyaminoamide can also be used in combination with another adjuvant, for example, 5% w/v polyaminoamide resin and 5% w/v tallow amine ethoxylate, thus reducing the requirement of additional adjuvants.

In another embodiment, the polyaminoamide resins and its derivatives may also be used as dispersants in oil dispersion (OD) formulations. Conventional dispersants used as dispersants in OD formulations are limited to solvent based polymeric dispersants. Initial screening of the modified and unmodified polyaminoamide resins shows effective dispersion of finely divided active ingredients in oil based systems.

The present invention further describes a method for making the composition. The method includes the step of contacting an electrolyte solution comprising a water-soluble active ingredient with a water-insoluble solid active ingredient and the dispersant.

For example, the method may be achieved by using traditional techniques to prepare SC's which involves; (i) mixing the water-insoluble solid active ingredient with the electrolyte solution containing the dispersant, (ii) wet milling the mixture with a homogenizer and (iii) bead milling the subsequent mixture to reduce the particle size of the water-insoluble solid active ingredient.

According to a second example, the claimed composition is obtained by adding the electrolyte solution including the dispersant to the milled SC.

According to a third example, the composition can be made by; (i) air milling the water-insoluble solid active ingredient, (ii) mixing the pre-milled ingredient to the electrolyte solution including the dispersant, and (iii) homogenizing the mixture.

According to a fourth example, the composition is obtained by: (i) formulating a WP or WG of the water-insoluble solid active ingredient, and (ii) adding the formulated WP or WG to the electrolyte solution containing the dispersant. The four examples are meant to be non-limiting examples to illustrate embodiments of the present invention.

Embodiments of the present invention may be useful as an agricultural or a veterinarian composition and can find application in formulations of biologically active ingredients. A "biologically active ingredient" as used herein is intended to include, without limitation: herbicides, insecticides, as well as fungicides. Other agriculturally active ingredients contemplated herein include biocides, molluscicides, algaicides, plant growth regulators, anthelmintics, rodenticides, nematocides, acaricides, amoebicides and protozoacides. Such ingredients are often generically referred to as pesticides. Also contemplated herein are crop safeners, insect repellants, fertilisers, micronutrient powders and adjuvants. The usefulness in formulations of such active ingredients may be best exemplified by the use of one or more biologically active ingredients such as a triazine in high electrolyte medium composed of glyphosate salt solution. In particular, it is often desirable that certain pesticides, which are in the form of a solid suspension or so called SC formulations, can be applied or co-formulated in a solution of an electrolyte. Such electrolytes may include water-soluble biologically active ingredients which are also pesticides, plant or insect growth modifiers or fertilizers. The precise amount of the active ingredient contained in the pesticide concentrate will depend upon the specific end-use application, for example, the target substrate to be treated or the area to be treated.

Embodiments of the present invention also disclose a method of treatment of vegetation comprising the step of contacting the agricultural compositions of the present invention to vegetation or soil. Herbicidal and fertilizer compositions of the present invention may be applied to plants and soils.

Further embodiments of the present invention also disclose a method of treatment of animals comprising the step of contacting the claimed composition to animals.

Embodiments of the present invention also disclose a method of treatment of a substrate comprising the step of contacting the compositions of the present invention to the substrate. Such examples may include public health uses of pesticides or animal health formulations. As an example, insecticides may be applied to floors and walls as a preventative treatment. Also, fungicides may be applied to seeds and soils. Compositions of the present invention may be used in other appropriate applications.

Embodiments of the present invention will be further illustrated by a consideration of the following examples, which are intended to be exemplary of the invention.

EXAMPLES a. Preparation of Polyaminoamide Derivatives

The Typical Procedure: The polyaminoamide resin was charged into the reactor with 0.35% by weight of a 50% by weight aqueous potassium hydroxide solution. The mixture was dehydrated to a water level of <0.1% w/w at 115-120° C. with nitrogen sparging for 90-120 minutes. The reactor was charged with polyoxyalkylene oxide.

Example 1

VERSAMID® 125 polyaminoamide (108 g, 1.08 amine equivalent) was mixed with propylene glycol (143 g), 50% by weight aqueous potassium hydroxide (0.88 g, 0.008 equivalent) and water (11 g). The mixture was heated to 110° C. and stirred for 30 minutes. A vacuum was applied to remove the water. After the (mild) dehydration was complete, ethylene oxide (113 g, 2.57 mol) was added over 45 minutes before allowing to react out for 60 minutes. The warm mix was diluted to 50% actives with water (See Table 1).

Examples 2-26

The 'Typical Procedure' as outlined above was used to generate Examples 2-26. Reaction conditions for preparing these polyaminoamide derivatives are summarized in Table 1.

Example 27

To a solution containing VERSAMID® 125 polyaminoamide (21.3 g, 0.20 amine equivalent) and propylene glycol (50 g) was added glycidol (19.5 g, 0.25 equivalent) under a nitrogen atmosphere. The solution was heated for 1 hour at 120° C. before addition of water (93.2 g) to the reaction mixture to give 21% actives.

Example 28

To a solution of VERSAMID®125 polyaminoamide (103 g), glycerine carbonate (111 g) was added slowly under a flow of nitrogen at 90° C. over 40 minutes. The reaction mixture was stirred at 90° C. for a further 45 minutes. Propylene glycol (200 g) was added to the hot mixture to give 52% actives.

b. Preparation of Formulations Comprising Polyaminoamide and Polyaminoamide Derivatives (Examples 1-28) in High Electrolyte Systems (i). Typical procedure for preparing a water-insoluble active ingredient dispersion in a high electrolyte system: The electrolyte (salt) solution and the dispersant which could be either the unmodified polyaminoamide resin or the polyaminoamide derivative outlined in Examples 1-28 or a commercially available dispersant, were combined. Pre air-milled solid active ingredient was added portionwise to the mixture under high shear. Water was added as the balance ingredient before the dispersion was fully homogenized under high shear once again.

(ii). Preparation of fully loaded formulations. The electrolyte (salt) solution and the dispersant which could be either the unmodified polyaminoamide resin or the polyaminoamide derivative outlined in Examples 1-28 or the commercial dispersant, humectant, structuring agent, silicon antifoam and adjuvant were combined. Pre air-milled water-insoluble solid active ingredient was added portionwise to the high electrolyte mixture under high shear. Water was added as the balance ingredient before the dispersion was fully homogenized under high shear once again.

(iii). Preparation of OD formulations. The oil and the dispersant which could be either the unmodified polyaminoamide resin or the polyaminoamide derivative outlined in Examples 1-28 and emulsifier/s were weighed into a beaker and stirred. Pre air-milled solid active ingredient was added portionwise to the mixture under high shear.

TABLE 1

Polyaminoamide derivatives

| Example | Starting material (SM) composition [Solvent] (V # = VERSAMID ® # polyaminoamide) | Nominal ratio of polyoxyalkylene oxide moles to "active hydrogens" | Weight ratio VERSAMID ® polyaminoamide:polyoxyalkylene oxide | Catalyst (KOH) conc (ppm) in SM | Reaction temp/time (° C./hr:min) | TAV (mgKOH/g)$^a$ |
|---|---|---|---|---|---|---|
| 1 | V 125 [Propylene Glycol]$^b$ | 2.4 Ethylene Oxide | 1:1 | 1700 | 115/0:35 | 74.3 |
| 2 | V 125 polyaminoamide [neat] | 2.4 Ethylene Oxide | 1:1 | 4200 | 115/1:10 | 162.0 |
| 3 | Example 2 | 4.8 Ethylene Oxide | 1:2.1 | 1960 | 125/0:45 | 118.2 |
| 4 | Example 3 | 9.0 Ethylene Oxide | 1:4.1 | 1960 | 125/3:43 | 76.8 |
| 5 | Example 4 | 20 Ethylene Oxide | 1:10 | 2700 | 142/6:50 | 40.3 |
| 6 | V 125 [neat] | 2.4 Propylene Oxide | 298:341 | 4200 | 135/6:45 | 148.3 |
| 7 | Example 6 | 2.4 Propylene Oxide + 2.4 Ethylene Oxide | 518:247 | 1960 | 152/~10:00 | 105.8 |
| 8 | Example 1 | 2.4 Ethylene Oxide + 2.4 Propylene Oxide | 375:252 | 7000 | ~135/0:27 | 68.3 |
| 9 | V 115 [neat] | 2.4 Ethylene Oxide | 330:240 | 6500 | 140-150/~9:00 | 144.3 |
| 10 | V 115 [Propylene Glycol]$^b$ | 2.4 Ethylene Oxide | 248:177 | 5200 | 125/1:20 | 90.9 |

TABLE 1-continued

Polyaminoamide derivatives

| Example | Starting material (SM) composition [Solvent] (V # = VERSAMID ® # polyaminoamide) | Nominal ratio of polyoxyalkylene oxide moles to "active hydrogens" | Weight ratio VERSAMID ® polyaminoamide:polyoxyalkylene oxide | Catalyst (KOH) conc (ppm) in SM | Reaction temp/time (° C./hr:min) | TAV (mgKOH/g)[a] |
|---|---|---|---|---|---|---|
| 11 | Example 10 | 4.8 Ethylene Oxide | 276:147 | 4300 | 125/0:45 | 74.7 |
| 12 | Example 11 | 10 Ethylene Oxide | 200:272 | 3400 | 125/1:13 | 53.0 |
| 13 | Example 12 | 15 Ethylene Oxide | 376:235 | 2300 | 125/0:30 | 39.0 |
| 14 | V 150 [Propylene Glycol][b] | 2.4 Ethylene Oxide | 257:303 | 5500 | 115-120/1:10 | 118.1 |
| 15 | Example 14 | 4.8 Ethylene Oxide | 447:260 | 4730 | 120/0:47 | 89.1 |
| 16 | Example 15 | 10 Ethylene Oxide | 810:430 | 4040 | 115/0:40 | 57.0 |
| 17 | Example 16 | 15 Ethylene Oxide | 900:336 | 2930 | 110/0:50 | 44.2 |
| 18 | V 140 [Propylene Glycol][b] | 2.4 Ethylene Oxide | 226:203 | 4450 | 115/2:00 | 123.8 |
| 19 | Example 18 | 4.8 Ethylene Oxide | 524:163 | 3080 | 110/0:30 | 90.1 |
| 20 | Example 19 | 10 Ethylene Oxide | 343:203 | 2350 | 112/0:40 | 61.1 |
| 21 | Example 20 | 15 Ethylene Oxide | 416:151 | 1400 | 106/2:30 | 46.6 |
| 22 | V 100 [Dipropylene Glycol] | 2.4 Ethylene Oxide | 112:31.5 | 3600 | 111/not relevant | 33.6[c] |
| 23 | Example 22 | 4.8 Ethylene Oxide | 315:30.6 | 3450 | 112/not relevant | 36.2 |
| 24 | Example 23 | 10 Ethylene Oxide | 296:56 | 3150 | 111/not relevant | 37.8 |
| 25 | Example 24 | 15 Ethylene Oxide | 278:38 | 2650 | 110/not relevant | 36.3 |
| 26 | Example 25 | 20 Ethylene Oxide | 240:58 | 2180 | 105/not relevant | 26.4 |
| 27 | V 125 [Propylene Glycol] | 1.25 Glycerol | — | — | 120/1 | — |
| 28 | V 125 | 1.25 Carbamate | — | — | 90/0:45 | — |

[a] Average Total Amine Value (TAV) reported.
[b] Equal weight of VERSAMID ® polyaminoamide and propylene glycol used.
[c] VERSAMID ® 100 polyaminoamide is a highly viscous substance which is insoluble in propylene glycol. DPG (dipropylene glycol) was used instead in a weight ratio of 1:2. Ethoxylation of the mixture afforded a product which separated into two layers.

Example 29

A composition according to teachings of the present invention was prepared by combining 35.0% by weight of glyphosate acid present as the isopropylamine salt, 3.9% by weight of the dispersant of Example 1 and 19.4% by weight of terbuthylazine according to the typical procedure outlined in section b (i) above.

Control Example 30

A comparison control composition was prepared by combining 35.0% by weight of glyphosate acid present as the isopropylamine salt, 3.9% by weight of a commercially available dispersant (TERSPERSE® 2500 dispersant available from Huntsman Corporation of The Woodlands, Tex.) and 19.4% by weight of terbuthylazine according to the typical procedure outlined in section b (i) above.

Example 31

A composition according to teachings of the present invention was prepared by combining 37.3% by weight of glyphosate acid present as the isopropylamine salt, 2.0% by weight of the dispersant of VERSAMID® 125 polyaminoamide and 15.5% by weight of terbuthylazine according to the typical procedure outlined in section b (i) above.

Example 32

A composition according to teachings of the present invention was prepared by combining 36.0% by weight of glyphosate acid present as the potassium salt, 5.0% by weight of the dispersant of Example 1 and 15.9% by weight of terbuthylazine according to the typical procedure outlined in section b (i) above.

Example 33

A composition according to teachings of the present invention was prepared by combining 29.5% by weight of glyphosate acid present as the potassium salt, 3.4% by weight of the dispersant of Example 1, 14.6% by weight of terbuthylazine, 8.2% by weight of TERWET® 3780 surfactant (commercially available from Huntsman Corporation of The Woodlands, Tex.,), 4.9% by weight of monoethyleneglycol, 0.3% of DOW CORNING® ANTIFOAM C emulsion (commercially available from Dow Corning Corporation) and 0.4% of VEEGUM® magnesium aluminium sulfate (commercially available from R.T. Vanderbilt Company, Inc. of Norwalk, Conn.) according to the typical procedure outlined in section b (ii) above.

Example 34

A composition according to teachings of the present invention was prepared by combining 24.2% by weight of glufosinate-ammonium (50% aqueous concentrate), 5.9% by weight of the dispersant of Example 27, 18.6% by weight of terbuthylazine, 9.7% by weight of EMPIMIN® KESM 70/AU surfactant (commercially available from the Huntsman Corporation of the Woodlands, Tex.), 0.5% of Antifoam C and 0.6% of AEROSIL® 200 fumed silica according to the typical procedure outlined in section b (ii) above.

Example 35

A composition according to teachings of the present invention was prepared by combining 20.0% by weight of terbuthylazine, 5.0% by weight of the dispersant of Example 1, 10.0% by weight of TERMUL® 3000 emulsifiers, 5% by weight of BENTONE GEL® IPM V rheological additive (commercially available from Elementis Specialties, Inc. of Hightstown, N.J.) and the balance of 70SN paraffin oil (commercially available from Kesri Oil Private Limited of Dehli, India) according to the typical procedure outlined in section b (iii) above.

Example 36

A composition according to teachings of the present invention was prepared by combining 33.7% by weight of glyphosate acid present as the isopropylamine salt, 4.0% by weight of the dispersant of Example 28 and 18.6% by weight of terbuthylazine according to the typical procedure outlined in section b (i) above.

Example 37

A composition according to teachings of the present invention was prepared by combining 36.6% by weight of glyphosate acid present as the isopropylamine salt, 2.0% by weight of the dispersant of Example 27 polyaminoamideand 20.0% by weight of simazine according to the typical procedure outlined in section b (i) above.

Example 38

A composition according to teachings of the present invention was prepared by combining 31.8% by weight of glyphosate acid present as the isopropylamine salt, 7.0% by weight of the dispersant of Example 28 and 23.7% by weight of sulfur according to the typical procedure outlined in section b (i) above.

c. Rheology Studies

By studying the rheological characteristics of a liquid composition containing a solid dispersed phase, one can investigate possible particle-particle interactions in the composition and estimate whether the composition will be prone to flocculation or can be stable at the given conditions.

The flow measurements of compositions prepared in Example 29 and Control Example 30 were performed using an AR 2000 Rheometer (from TA Instruments, Inc. of New Castle, Del.). The compositions were loaded onto the rheometer and left to equilibrate for 2 minutes at 20° C. before starting the measurement. The flow was measured by controlling the shear rate from 0 to 100 s$^{-1}$ rate up in 2 minutes at 20° C., a peak hold step at 100 s$^{-1}$ for 1 minute and rate down from 100 to 0 s$^{-1}$ in 1 minute.

Figure 1:
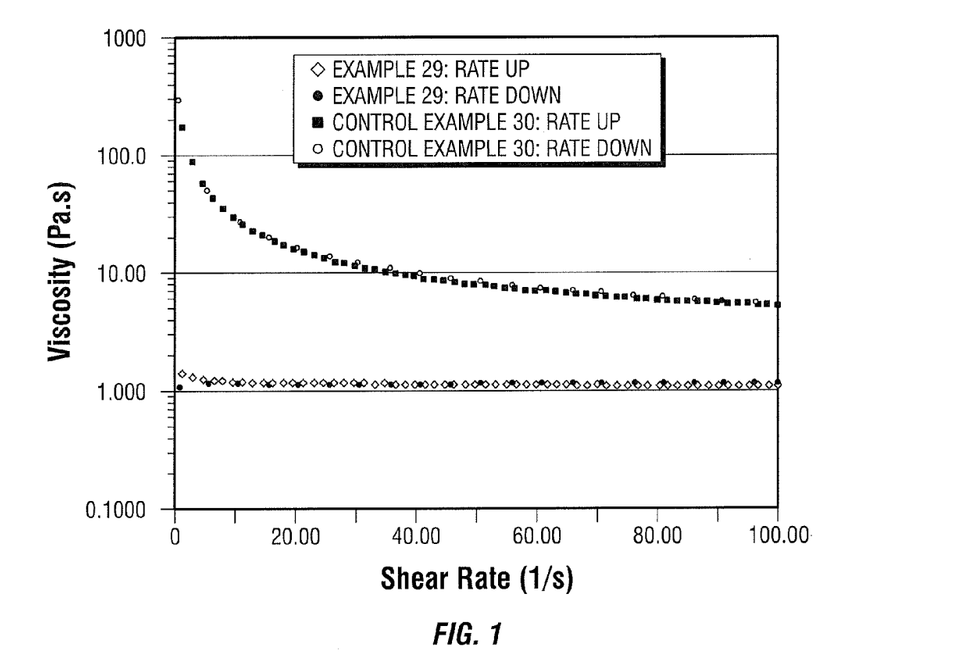
FIG. 1 is a graph representing the rheological properties, in particular the viscosity profile, of an embodiment of the present invention compared with a current commercial dispersant.

Rheological Behaviour of the Composition: Example 29 versus Control Example 30. Example 29, when compared with the Control Example 30, demonstrated superior rheological properties. In particular, Example 29 afforded a phase stable solution which exhibited a lower viscosity compared with the Control Example 30. The Control Example 30 showed strong shear thinning behaviour and a significant yield stress, which is indicative of flocculation in a preparation containing no structuring aid, while the viscosity profile of the claimed composition has changed little over the applied shear rate and showed only a minor yield stress (See FIG. 1).

Figure 2:
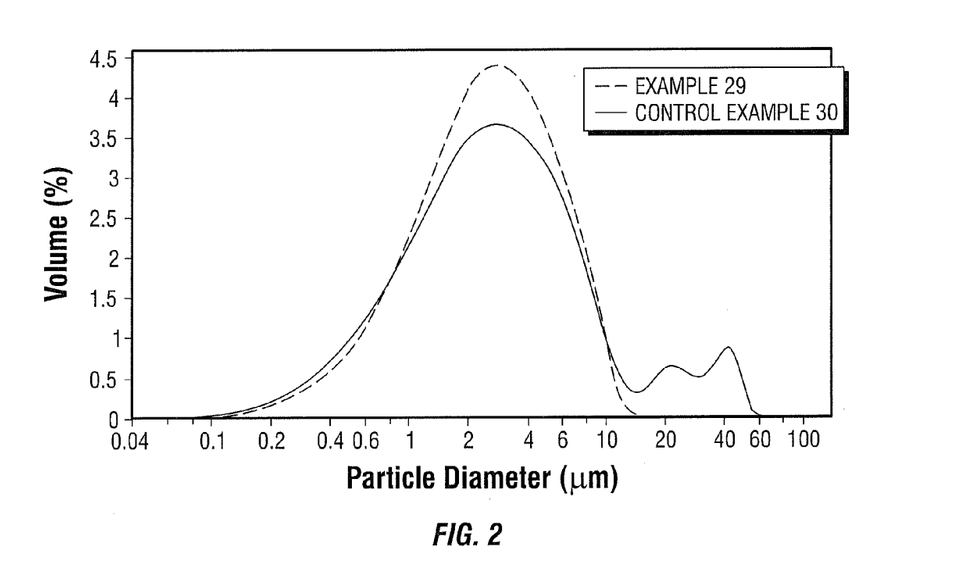
FIG. 2 is a graph charting particle size distribution of an embodiment of the present invention compared with a current commercial dispersant.

The measurements are indicative of a good dispersion in case of the Example 29 (an embodiment of the present invention), whereas evidence of flocculation is seen for the Control Example 30. The particle size distribution of the finalized formulations (See FIG. 2 and Table 2) provide additional evidence for the solid active ingredient in the electrolyte (salt) solution to be effectively dispersed in the composition containing the polyaminoamide derivative.

TABLE 2

Particle size distribution of compositions Example 29 and Control Example 30

| Composition | Mean (μm) | D10 (μm) | D50 (μm) | D90 (μm) |
|---|---|---|---|---|
| Example 29 | 2.33 | 0.757 | 2.52 | 6.56 |
| Control Example 30 | 2.76 | 0.688 | 2.7 | 10.4 |

The flow measurement of composition prepared in Example 36 (FIG. 3) was performed using an AR 2000 Rheometer (from TA Instruments, Inc. of New Castle, Del.). The compositions were loaded onto the rheometer and left to equilibrate for 2 minutes at 20° C. before starting the measurement. The flow was measured by controlling the shear rate from 0 to 100 s$^{-1}$ rate up in 2 minute at 20° C., a peak hold step at 100 s$^{-1}$ for 1 minute and rate down from 100 to 0 s$^{-1}$ in 1 minute.

Figure 3:
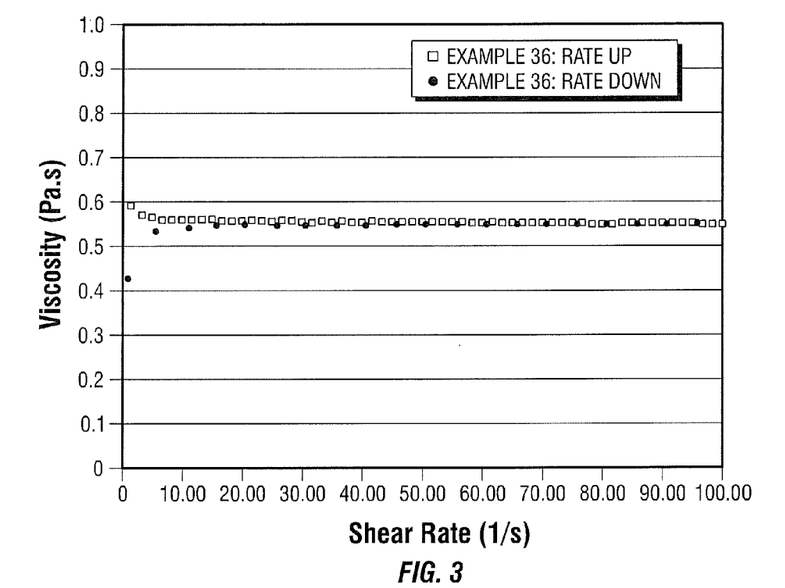
FIG. 3 is a graph representing the rheological properties, in particular the viscosity profile, of an embodiment of the present invention.

Example 36 (an embodiment of the present invention) has demonstrated a low and practically constant viscosity in the chosen shear rate range, which is indicative of a well dispersed system.

The flow measurement of composition prepared in Example 37 (FIG. 4) was performed using an AR 2000 Rheometer (from TA Instruments, Inc. of New Castle, Del.). The compositions were loaded onto the rheometer and left to equilibrate for 2 minutes at 20° C. before starting the measurement. The flow was measured by controlling the shear rate from 0 to 50 s$^{-1}$ rate up in 2 minutes at 20° C., a peak hold step at 50 s$^{-1}$ for 1 minute and rate down from 50 to 0 s$^{-1}$ in 1 minute.

Figure 4:
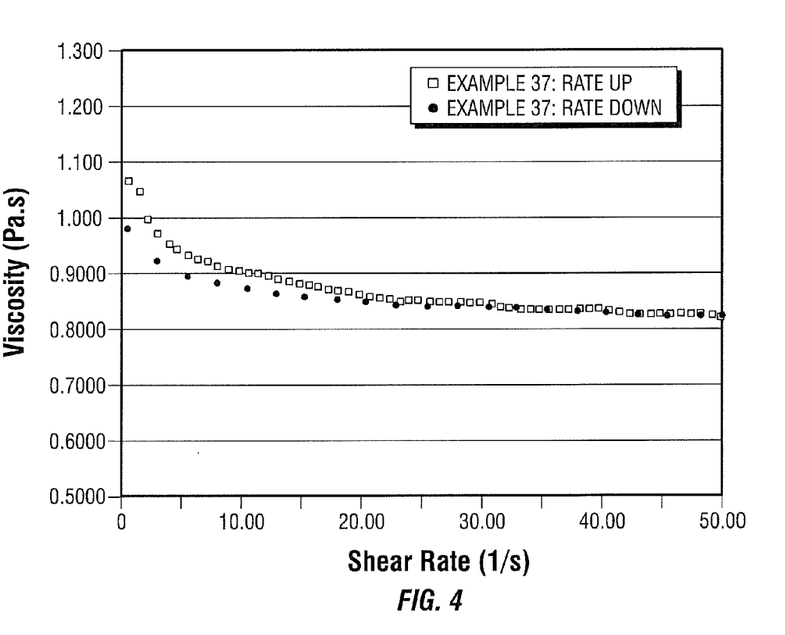
FIG. 4 is a graph representing the rheological properties, in particular the viscosity profile, of an embodiment of the present invention.

Example 37 (an embodiment of the present invention) has demonstrated a low viscosity and only minor shear thinning behaviour in the chosen shear rate range, which is indicative of a well dispersed system.

The flow measurement of composition prepared in Example 38 (FIG. 5) was performed using an AR 2000 Rheometer (from TA Instruments, Inc. of New Castle, Del.). The compositions were loaded onto the rheometer and left to equilibrate for 2 minutes at 20° C. before starting the measurement. The flow was measured by controlling the shear rate from 0 to 100 s$^{-1}$ rate up in 2 minutes at 20° C., a peak hold step at 100 s$^{-1}$ for 1 minute and rate down from 100 to 0 s$^{-1}$.

Figure 5:
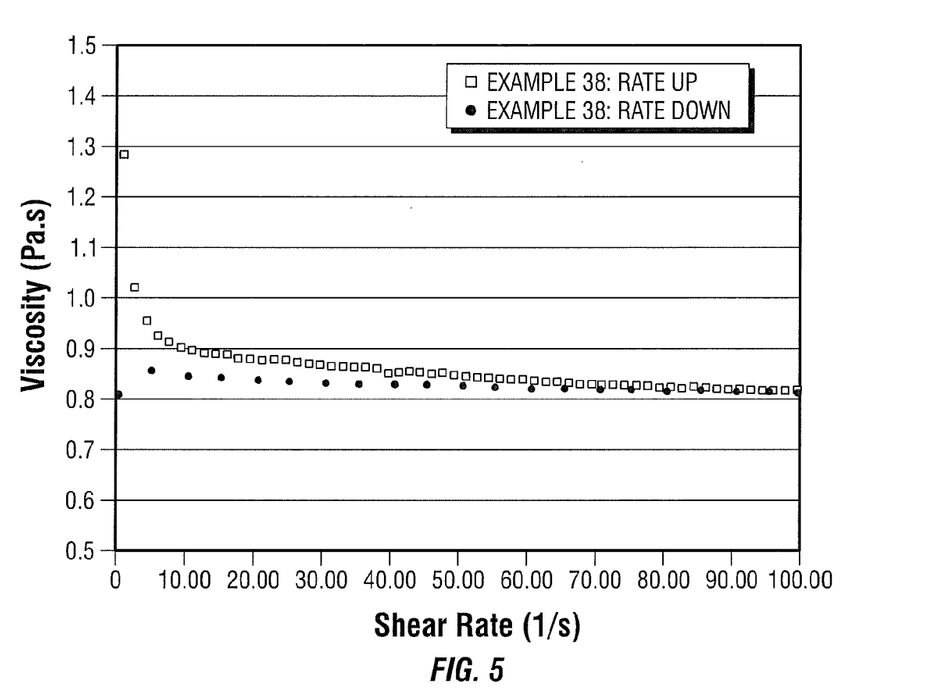
FIG. 5 is a graph representing the rheological properties, in particular the viscosity profile, of an embodiment of the present invention.

Example 38 (an embodiment of the present invention) has demonstrated a low viscosity and only minor shear thinning behaviour in the chosen shear rate range, which is indicative of a well dispersed system.

d. Bioefficacy Performance

Sample preparation. Two sample solutions according to teachings of the present invention were prepared by dissolving either Example 1 or Example 27 (100% active equivalent) in 450 grams acid equivalent per liter (gae/L) glyphosate present as the potassium salt. One control sample was untreated and a second "commercial control" sample used a commercially available herbicided (ROUNDUP® CT broadacre herbicide).

Plant propagation. Oat seeds were sown to 3 cm depth and variegated thistle was sown to 1 cm depth in 10 cm diameter pots filled with potting mix (according to Australian Standard AS 3743 (2002)). One week after seedling emergence, seedlings were thinned for uniform size to one seedling per pot. Oats were grown in a temperature-controlled greenhouse (14° C.-25° C.) for 8 days then outdoors for 13 days prior to spray application, to more closely simulate field conditions. Variegated thistle was grown in a temperature-controlled greenhouse (14° C.-25° C.) for 14 days then outdoors for 23 days prior to spray application. After the application of herbicides the pots were returned to the greenhouse until harvested for fresh weight.

Herbicide application. Herbicide formulations were applied using an enclosed laboratory track-sprayer fitted with three 110° flat fan nozzles (Teejet XR11001-VS available under the tradename JOHN DEERE® sprayer parts from the Deere and Company of Moline, Ill.) spaced at 50 cm intervals across the boom. The boom moved along a fixed track at 6 kilometers hour$^{-1}$, sprayed at a water volume of 64 liters hectare$^{-1}$ with a pressure of 200 kilopascals.

Assessment. Visual observations of % control were recorded 10 Days After Treatment (DAT) or 12 DAT. Seedlings were harvested by cutting foliage off at base immediately prior to weighing on a Sartorius Basic electronic balance (range 0-4100 grams, commercially available from Satorius AG of Goettingen, Germany) 14 DAT.

Statistical analysis. Data was analyzed using a factorial design with two factors, formulation and rate. A 5% least significant differences (LSD) weal calculated for the mean of each treatment. The greatest herbicidal effect is denoted with alpha code "a" when significantly different to other treatments, which are coded "b", "c", "d" etc. with decreasing effect.

TABLE 3

Effect of glyphosate treatment on variegated thistle and oat weed species

| Sample | Fresh Weight Formulation Mean | |
| --- | --- | --- |
|  | Variegated Thistle | Oat |
| Untreated Control | 18.30 | 4.28 |
| Commercial Control | 6.66 b-e | 1.69 ab |
| Example 1 | 7.03 cde | 2.99 f |
| Example 27 | 6.76 b-e | 3.05 f |

Table 3 shows that Examples 1 and 27 have comparable bioefficacy as the Commercial Control in variegated thistle. Examples 1 and 27 additionally show some adjuvancy effects in the oat species when compared to the Untreated Control. In this table, a low value is indicative of high efficacy in comparison to the Untreated Control.

Those skilled in the art will appreciate that the invention described herein is susceptible to variations and modifications other than those specifically described. It is to be understood that the invention includes all such variations and modifications which fall within its spirit and scope. The invention also includes all the steps, features, compositions and compounds referred to or indicated in this specification, individually or collectively, and any and all combinations of any two or more of said steps or features.

What is claimed is:

1. A composition comprising:
   an electrolyte solution having a water-soluble active ingredient;
   a water-insoluble solid active ingredient selected from the group consisting of a pesticide, a herbicide, an insecticide, an insect repellent, a fungicide, a bactericide, a plant growth regulator, a fertilizer, an acaricide, an anthelmintic, a nematicide, and a combination thereof;
   a dispersant selected from the group consisting of a polyoxyalkylene derivative of a polyaminoamide resin, wherein the polyaminoamide resin is obtained by thermal condensation of a poly-functional fatty acid with a poly-functional amine and wherein a starting acid for the poly-functional fatty acid is a $C_2$ to a $C_{60}$ fatty acid; and
   wherein the polyoxyalkylene derivative is obtained by reacting the polyaminoamide resin with a polyoxyalkylene selected from the group consisting of ethylene oxide, propylene oxide and a mixture thereof at a molar ratio of polyoxyalkylene to polyaminoamide active hydrogens from 2.4 to 4.8;
   wherein the weight ratio of the dispersant to the water-insoluble solid active ingredient is from 1:50 to 1:5, and the weight ratio of the electrolyte in solution to the water-insoluble solid active ingredient is from 60:1 to 1:1.

2. The composition of claim 1, wherein the concentration of the water-soluble active ingredient is greater than 3% by weight of the composition.

3. The composition of claim 1, wherein the composition is an agricultural or veterinarian composition.

4. The composition of claim 1, wherein the poly-functional amine is selected from the group consisting of: a $C_2$ to a $C_{10}$ alkylene diamine, a dimer diamine, a polyoxyalkyleneamine, an ethyleneamine and a combination thereof.

5. The composition of claim 4, wherein the ethyleneamine is selected from the group consisting of: an ethylenediamine, a diethylenetriamine, a triethylenetetramine, a tetraethylenepentamine and a combination thereof.

6. The composition of claim 1, wherein the polyoxyalkylene derivative of the polyaminoamide resin is obtained by an alkoxylation reaction.

7. The composition of claim 1 further comprising at least one additive selected from the group consisting of: a humectant, a thickener, a wetting agent, an adjuvant, a stabilizer, a safener, a structuring agent, an antifoam, a pigment, a dye, a stench, an emetic, a filler, a carrier, a buffer and a combination thereof.

8. A method of treating vegetation comprising the step of applying the composition according to claim 1 to vegetation or soil.

* * * * *